(12) United States Patent
Bulut et al.

(10) Patent No.: US 11,586,768 B2
(45) Date of Patent: Feb. 21, 2023

(54) PRIVACY ENSURING PERSONAL HEALTH RECORD DATA SHARING

(71) Applicant: KONINKLIJKE PHILIPS N.V., Eindhoven (NL)

(72) Inventors: Murtaza Bulut, Eindhoven (NL); Mark Anthony Hennessy, Eersel (NL); Mark Thomas Johnson, Arendonk (NL); Vincentius Paulus Buil, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 188 days.

(21) Appl. No.: 16/899,646

(22) Filed: Jun. 12, 2020

(65) Prior Publication Data

US 2020/0394334 A1 Dec. 17, 2020

Related U.S. Application Data

(60) Provisional application No. 62/860,966, filed on Jun. 13, 2019.

(51) Int. Cl.
*G06F 21/62* (2013.01)
*G16H 10/60* (2018.01)
*G06N 5/048* (2023.01)
*G16H 50/20* (2018.01)

(52) U.S. Cl.
CPC ......... *G06F 21/6254* (2013.01); *G06N 5/048* (2013.01); *G16H 10/60* (2018.01); *G16H 50/20* (2018.01)

(58) Field of Classification Search
CPC .... G06F 21/6254; G16H 10/60; G16H 50/20; G06N 5/048
See application file for complete search history.

(56) References Cited

U.S. PATENT DOCUMENTS

| | | | |
|---|---|---|---|
| 9,497,170 B2 * | 11/2016 | Akiyama | H04L 63/0421 |
| 9,973,455 B1 | 5/2018 | Fowler | |
| 10,566,082 B1 * | 2/2020 | McNair | G06Q 50/22 |
| 10,635,837 B1 * | 4/2020 | Jun | G16H 10/60 |
| 10,885,170 B1 * | 1/2021 | Maliani | H04L 9/0637 |

(Continued)

FOREIGN PATENT DOCUMENTS

WO 2004017164 A2 2/2004

OTHER PUBLICATIONS

International Search Report and Written Opinion dated Jul. 31, 2020 for International Application No. PCT/EP2020/066281 Jun. 12, 2020.

(Continued)

*Primary Examiner* — Joseph P Hirl
*Assistant Examiner* — Stephen T Gundry

(57) ABSTRACT

A computer-implemented method that receives at an apparatus a request from a first computing device for access to information related to a first user data set; determines, or receives an indication of a determination, whether the first computing device can access the information based on criteria for sharing information, the criteria based on one or more characteristics of the first user data set and a second user data set accessible by the first computing device; and provide a response based on the determination, the response preserving privacy of a user corresponding to the first user data set.

23 Claims, 7 Drawing Sheets

(56) References Cited

U.S. PATENT DOCUMENTS

| | | | | |
|---|---|---|---|---|
| 11,055,737 | B1* | 7/2021 | Dakic | G06V 10/764 |
| 11,106,692 | B1* | 8/2021 | Guetta | G06F 16/248 |
| 11,217,332 | B1* | 1/2022 | Bryant | G07C 5/008 |
| 11,238,493 | B1* | 2/2022 | Dakic | G16H 20/10 |
| 2002/0010679 | A1 | 1/2002 | Felsher | |
| 2013/0197939 | A1* | 8/2013 | Shah | G16H 10/60 |
| | | | | 705/3 |
| 2014/0298030 | A1* | 10/2014 | Akiyama | H04L 63/062 |
| | | | | 713/172 |
| 2015/0149208 | A1* | 5/2015 | Lynch | G16H 10/60 |
| | | | | 705/3 |
| 2015/0363603 | A1* | 12/2015 | Hsu | G06F 21/62 |
| | | | | 707/783 |
| 2016/0132686 | A1* | 5/2016 | Peng | G06F 21/604 |
| | | | | 726/28 |
| 2016/0147758 | A1* | 5/2016 | Chhaya | G06F 16/437 |
| | | | | 707/733 |
| 2016/0147945 | A1 | 5/2016 | Maccarthy | |
| 2016/0277374 | A1 | 9/2016 | Reid et al. | |
| 2017/0039242 | A1* | 2/2017 | Milton | H04W 4/02 |
| 2017/0083719 | A1* | 3/2017 | Scaiano | G06F 21/6254 |
| 2017/0091397 | A1* | 3/2017 | Shah | G16H 10/60 |
| 2017/0346693 | A1* | 11/2017 | Dix | H04L 9/3247 |
| 2018/0197638 | A1 | 7/2018 | Blanshard et al. | |
| 2020/0097910 | A1* | 3/2020 | Krasnov | G16H 40/67 |
| 2020/0226285 | A1* | 7/2020 | Bulleit | G16H 40/67 |
| 2020/0227160 | A1* | 7/2020 | Youngblood | G16H 40/67 |
| 2020/0302319 | A1* | 9/2020 | Dawson | G06N 5/048 |
| 2020/0374104 | A1* | 11/2020 | Heath | G06F 16/2379 |
| 2020/0401727 | A1* | 12/2020 | Hennessy | G16H 10/60 |
| 2020/0402625 | A1* | 12/2020 | Aravamudan | G06F 21/64 |
| 2021/0005324 | A1* | 1/2021 | Bostic | G16H 50/20 |
| 2021/0183505 | A1* | 6/2021 | Velaga | G06Q 20/14 |
| 2021/0240720 | A1* | 8/2021 | Muse | G06F 16/24573 |
| 2021/0248268 | A1* | 8/2021 | Ardhanari | G06N 3/0472 |
| 2021/0257088 | A1* | 8/2021 | Melchionne | G16H 40/20 |
| 2021/0264054 | A1* | 8/2021 | Anson | G06F 21/725 |
| 2021/0286891 | A1* | 9/2021 | Sislow | G06F 21/6245 |
| 2021/0350357 | A1* | 11/2021 | Lafontaine | G06Q 20/401 |
| 2022/0027440 | A1* | 1/2022 | Brannon | G06F 11/3438 |
| 2022/0035896 | A1* | 2/2022 | Brannon | G06F 11/3438 |
| 2022/0036377 | A1* | 2/2022 | Seibel | G06Q 30/08 |
| 2022/0050921 | A1* | 2/2022 | LaFever | H04L 9/0891 |
| 2022/0092495 | A1* | 3/2022 | Brannon | H04L 63/102 |
| 2022/0093248 | A1* | 3/2022 | Amisano | G16H 50/70 |
| 2022/0101966 | A1* | 3/2022 | Goldstein | G16H 10/60 |

OTHER PUBLICATIONS

Anonymous, "Personal health record", https://en.wikipedia.org/w/index.php?title=Personal_health_record&oldid=836776277, Accessed Jun. 9, 2020.

Patel, V. et al., "The Role of Health Care Experience and Consumer Information Efficacy in Shaping Privacy and Security Perceptions of Medical Records: National Consumer Survey Results", JMIR Med Inform 2015;3(2):e14.

Anonymous, "Secure multi-party computation", https://en.wikipedia.org/wiki/Secure_multi-party_computation, Accessed Jun. 9, 2020.

Anonymous, "Garbled circuit", https://en.wikipedia.org/wiki/Garbled_circuit, Accessed Jun. 9, 2020.

Anonymous, "Trusted execution environment", https://en.wikipedia.org/wiki/Trusted_execution_environment, Accessed Jun. 9, 2020.

* cited by examiner

PRIVACY ENSURING PERSONAL HEALTH RECORD DATA SHARING

CROSS-REFERENCE TO PRIOR APPLICATIONS

This application claims the benefit of U.S. Provisional Application No. 62/860,966, filed on 13 Jun. 2019. This application is hereby incorporated by reference herein.

FIELD OF THE INVENTION

The present invention is generally related to data privacy, and more particularly, privacy in health record sharing among providers.

BACKGROUND OF THE INVENTION

A Personal Health Record (PHR) is a health record where health data and information related to the care of a person is maintained by his or herself (hereinafter, the male pronoun is used with the understanding that both genders may apply). A PHR may be viewed as a system of records for the health of the person, and includes data sharing controls regarding with whom the data is shared. The kinds of data stored in a PHR is quite broad, and includes information about their allergies, adverse drug reactions, family medical history, any chronic diseases, illnesses and hospitalizations, lab results, imaging reports (e.g. X-Rays, CT scans etc.), prescription records, medications and dosages, vaccinations, surgeries, observations of daily living, and/or any personally collected health data from health data sources (e.g., personal health devices, social media sources, etc.).

From an architectural point of view, a PHR may be perceived as a storage and access control layer, where the data format/semantics of patient data is normalized. Then, applications can be built on top of this storage layer. In practice, there needs to be a large infrastructure behind the PHR, as connectivity to the electronic health records (EHRs) of health care providers is needed to populate the PHR with up-to-date health data of the patient such that those data sources can be trusted, and the provenance of the data is maintained. Stakeholders who may have an interest in a PHR include the patient themselves, healthcare providers wanting to provide safer healthcare, and/or insurance companies whom want to have an accurate view of how the patient is being treated to be able to verify insurance claims.

A patient may receive care from multiple healthcare providers, and hence multiple EHRs may be present among the corresponding providers, the EHRs serving as a source of data not only for a patient's PHR but also potentially for data sharing between the providers. Customer survey data research published by the 2015 *Journal of Medical Internet Research Medical Informatics* ("The Role of Health Care Experience and Consumer Information Efficacy in Shaping Privacy and Security Perceptions of Medical Records: National Consumer Survey Results") shows some patients have concerns when it comes to data sharing between providers. In other words, one problem with data sharing among providers is that of privacy concerns among patients. One way to solve this problem is simply to prevent data from being shared. However, this may not be desirable, or possible, as this can prevent the patient from receiving proper care. Furthermore, sharing of data (e.g., via cohorts) is also needed to carry out clinical or academic investigations.

Another approach to the problem is to allow healthcare providers to share data, but only after each healthcare provider separately (e.g., individually) anonymizes the data they possess or control. Although this process ensures patient privacy within an individual ecosystem of each healthcare provider, such an approach may still lead to a patient's privacy being compromised, as different healthcare providers may have different pieces of patient data, which when combined may lead to the patient being identified. In other words, combining anonymized data from one healthcare provider, say HCP1, and from another healthcare provider, say HCP2 (e.g., where the anonymization was done only concerning the patient data in the HCP1 and HCP2 ecosystem, respectively) may still make the patient identifiable. For example, HCP1 (e.g., a hospital) may have a data set (e.g., name, electrocardiography (ECG) results, diagnosis, and age) for a cohort of patients (e.g., employees of company X), and HCP2 (e.g., an insurance company) may have a data set (e.g., name, age, and address) for the same cohort. In this example, HCP2 requests data from HCP1, which anonymizes the data by removing the name field and then shares with HCP2. But suppose there is only a single person with an age of thirty-three (33) years, and based on this fact, HCP2 can now identify the person that has an Atrial Fibrillation (AF) disease, using the data it had received from HCP1. In other words, anonymization of data individually by each healthcare provider may not be sufficient to ensure the privacy of the user. Therefore, there is a need for an additional check and verifications when data is to be shared among multiple providers.

One approach to carrying out an additional check/verification is through the use of a $3^{rd}$ party service provider that is trusted and receives the data to be shared from two healthcare providers, and checks that the combination of data still contains no personal, identifiable data, and then releases the data to the requesting healthcare provider. This function is usually achieved by both healthcare providers releasing their individually, anonymized data along with a pseudo-identifier representing a single patient to the trusted $3^{rd}$ party. While the $3^{rd}$ party might be trusted and ethical, one problem is that the storing of such combinations of data may be vulnerable to data breaches/hacking. There needs to be a level of trust and confidence that the $3^{rd}$ party implements good procedures on managing such data combinations internally. Ultimately, this kind of $3^{rd}$ party data governance is expensive to provide, leading to added costs to doing research.

SUMMARY OF THE INVENTION

One object of the present invention is to ensure the privacy of user data when the user data is shared among healthcare providers. To better address such concerns, in a first aspect of the invention, a system and computer-implemented method is disclosed that receives, at an apparatus comprising one or more processors configured by instructions, a request from a first computing device for access to information related to a first user data set, determines, or receives an indication of a determination, whether the first computing device can access the information based on criteria for sharing information, the criteria based on one or more characteristics of the first user data set and a second user data set accessible by the first computing device; and provide a response based on the determination, the response preserving privacy of a user corresponding to the first user data set. By performing various checks, according to the criteria at different stages of processing, based on a request for data to be shared, the patient's identity remains anonymous.

In one embodiment, wherein the criteria comprises commonality of one or more users associated with the first user data set and the second user data set according to a first likelihood function, wherein the one or more processors are configured by the instructions to determine, or receive the indication of the determination, by: determining, alone or in combination with one or more other devices, or receiving an indication of a determination from the one or more other devices, whether according to the first likelihood function there is a presence of at least one common user among the first user data set and the second user data set, wherein the determination or receipt of the indication of the determination is based on computations performed on an anonymized version of the first and second user data sets. The anonymization of the user data may not be sufficient to protect a patient's privacy, and hence determining, or receiving an indication of the determination (e.g., an indication from another device that performs the determination and sends the indication in the form of a warning/message, flag, bit setting, etc.) of a patient or patients that are common (e.g., based on a likelihood function, for instance where that patient falls within the range between 0 [no presence] and 1 [certain presence], including via the use of a thresholding function) to both sets of data provides an added security check to ensure patient privacy is not compromised by a combination of data sets from multiple entities. Likelihood may be computed as a result of analyzing and/or classifying (e.g., determining a likelihood of belonging to a certain class and then processing to determine the class to be assigned, though in some embodiments, a likelihood function may be computed without classification, including by directly using the available data/information) the user data sets.

In one embodiment, the one or more processors are configured by the instructions to determine, or receive an indication of a determination, whether the first computing device can access the information further based on additional criteria, wherein the additional criteria comprises identification from the first and second user data sets of the at least one common user according to a second likelihood function. The criteria further includes the likelihood or risk of identification, and hence another level of security is used to determine whether, despite the commonality of a patient among the data sets, there a likelihood or risk of identifying the patient. This added check provides for an efficient security measure that also benefits the requester of data (and hence may facilitate research) by not excluding, outright, a requested data sharing when a patient is merely common to multiple data sets yet unidentifiable.

In one embodiment, wherein the response comprises one of: a denial of the request; removal or denial of access of data corresponding to an identifiable user or users from the first user data set, the removal implemented before sharing; removal of a first field of data corresponding to the identifiable user or users from the first user data set, the first field of data comprising a portion that permits the user to be identifiable, the removal implemented before sharing; transmittal of a request to the first computing device for removal of data corresponding to the identifiable user or users from the second user data set, the removal implemented before sharing; transmittal of a request to the first computing device for removal of a second field of data corresponding to the identifiable user or users from the second user data set, the second field of data comprising a portion that permits the user to be identifiable, the removal implemented before sharing; or permitting access to the information based on the criteria comprising consent or permission by the user to access the information. The available mechanisms for handling a request when there is a risk of compromising patient identity include actions on the part of the requester or recipient of the request, providing a level of flexibility in handling of data sharing requests. Further, cases or scenarios may arise where denial of a request (for data sharing) may be preferred over denial of access as a stronger security measure. For example, if one healthcare provider suspects that another healthcare provider may "trick" computations of commonality/identifiability, then denial of the request may be preferred. Or, in cases where one healthcare provider requests information from two other healthcare providers, then one of those two recipients of the request may decide to deny the request before the other data request or transfer is settled.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF EMBODIMENTS

Figure 1:
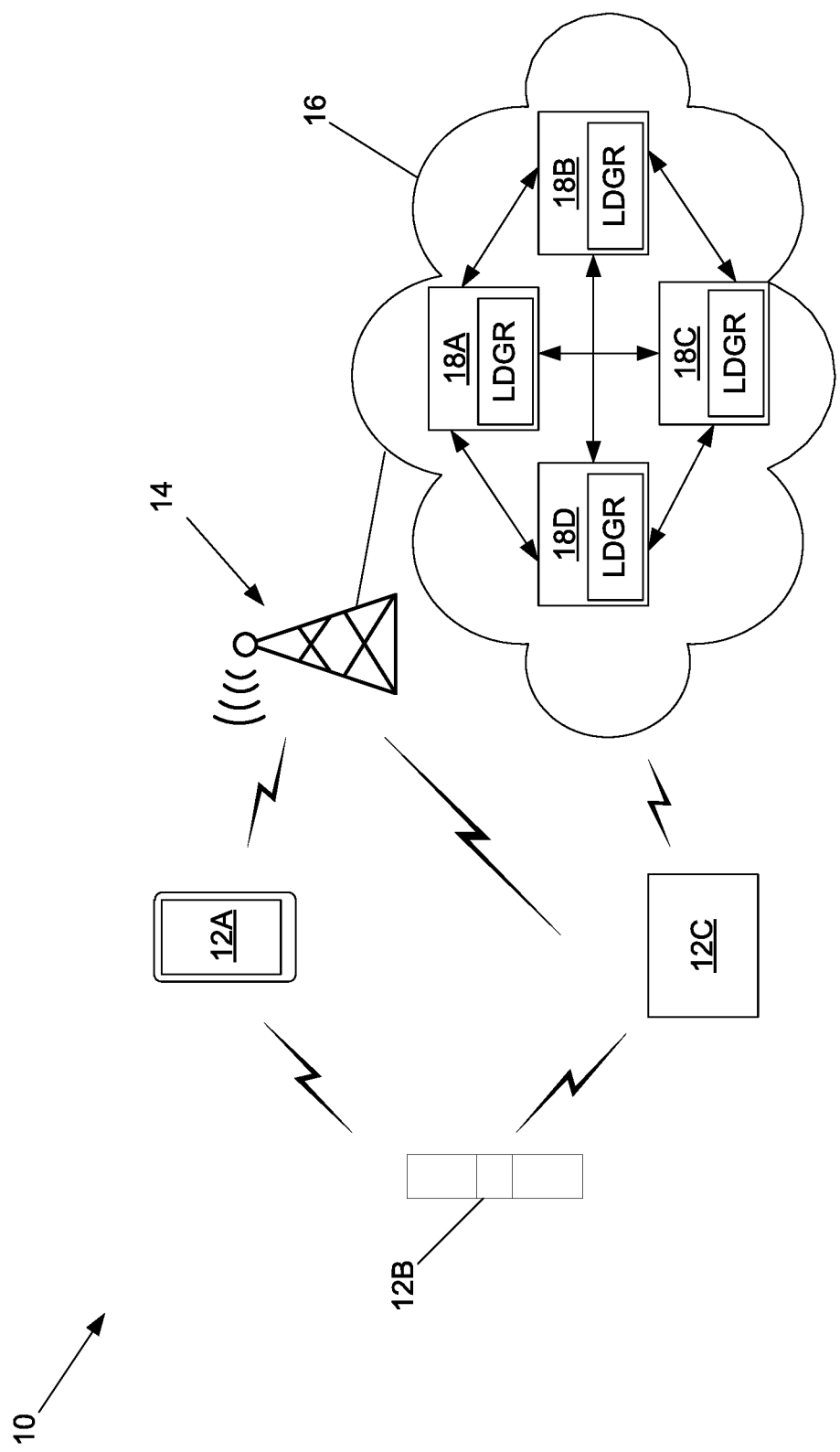
FIG. 1 is a schematic diagram that illustrates an example environment in which a data privacy sharing system is used, in accordance with an embodiment of the invention.

Disclosed herein are certain embodiments of a data privacy sharing system and method (collectively hereinafter referred to as a data privacy sharing system) that comprises functionality that uses criteria based on one or more characteristics of user data sets to share data in a manner that preserves the privacy of the user(s) corresponding to the shared data. In one embodiment, the data privacy sharing system comprises an apparatus for one healthcare provider that receives a request for data corresponding to a user or group of users (e.g., cohorts), the request sent by another healthcare provider. The apparatus, using various criteria, performs various checks at different data and/or security levels to ensure that the patient (or user, where patient and user are used interchangeably throughout) remains anonymous.

Digressing briefly, past approaches include the anonymization of user data prior to sharing and/or the use of trusted $3^{rd}$ parties to ensure an individual's identity is not discovered, yet problems may still arise when a healthcare provider (or trusted $3^{rd}$ party) is in possession of data sets where the combination of data sets may give rise to a patient's identity. Through use of certain embodiments of a data privacy sharing system, the privacy of a patient is preserved without requiring a $3^{rd}$ party or, if a $3^{rd}$ party is used, expending the cost in ensuring compliance by the $3^{rd}$ party. Note that the terms $3^{rd}$ party and third party are used interchangeably throughout.

Having summarized certain features of a data privacy sharing system of the present disclosure, reference will now be made in detail to the description of a data privacy sharing system as illustrated in the drawings. While a data privacy sharing system will be described in connection with these drawings, there is no intent to limit it to the embodiment or embodiments disclosed herein. Further, although the description identifies or describes specifics of one or more embodiments, such specifics are not necessarily part of every embodiment, nor are all of any various stated advantages necessarily associated with a single embodiment. The intent is to cover all alternatives, modifications and equivalents included within the principles and scope of the disclosure as defined by the appended claims. For instance, though the description that follows emphasizes healthcare providers in the form of hospital or physician services, research institutions or other institutions, including third party institutions, that share private data are also contemplated and considered to be within the scope of the disclosure. Further, it should be appreciated by one having ordinary skill in the art, in the context of the present disclosure, that certain embodiments of a data privacy sharing system may be utilized in other applications and/or with other and/or additional entities where concerns of data privacy in information sharing is present, including data sharing involving any combination of healthcare providers, insurance companies, retail stores (e.g., possess data of customers that may be common), governments, social media (e.g., LinkedIn®, Facebook, etc.), schools (e.g., where student have transferred), companies, employers, etc. As another example, two or more embodiments may be interchanged or combined in any combination. Further, it should be appreciated in the context of the present disclosure that the claims are not necessarily limited to the particular embodiments set out in the description.

In the description that follows, terminology that implies or expresses action by a healthcare provider is understood to refer to an implementation via a corresponding computing device or devices that acts with or without administrator/user intervention.

Referring now to FIG. 1, shown is an example environment 10 in which certain embodiments of a data privacy sharing system may be implemented. It should be appreciated by one having ordinary skill in the art in the context of the present disclosure that the environment 10 is one example among many, and that some embodiments of a data privacy sharing system may be used in environments with fewer, greater, and/or different components than those depicted in FIG. 1. The data privacy sharing system may comprise all of the devices depicted in FIG. 1 in one embodiment, or a subset of the depicted device in some embodiments. The environment 10 comprises a plurality of devices that enable communication of information throughout one or more networks. The depicted environment 10 comprises one or more user devices 12 (e.g., 12A, 12B, and 12C), a wireless/cellular network 14, and a network 16, which may include plural computing devices 18 (e.g., 18A, 18B, 18C, 18D, etc.) communicatively coupled to each other and to the user devices 12. In one embodiment, the network 16 comprises a peer-to-peer blockchain network, which comprises a decentralized network of computing devices 18 or nodes that each comprises a copy of a blockchain. In some embodiments, the network 16 may comprise a cloud network or server farm arranged in a peer-to-peer or master/slave configuration. The computing devices 18 may each be associated with a respective healthcare provider (including a third party device that serves the healthcare providers), or two or more of the computing devices 18 may collectively be associated with a respective healthcare provider, where data for each patient may be stored (e.g., as an electronic health record or EHR) at each respective computing device 18 or at a main computing device serving as the main repository for a group of computing devices on a network. In some embodiments, the computing devices 18 may include a third party device(s) configured to store the personal health records (PHRs) of patients and/or provide storage and/or computation capabilities in whole or in part for data privacy sharing services on behalf of the other healthcare providers devices 18. The network 16 may further include one or more additional networks, including a wide area network (WAN), metropolitan area network (MAN), one or more local area networks (LANs), among other networks.

The user devices 12 comprise one of a plurality of types of devices, including a smartphone 12A, wearable device or activity tracker 12B, laptop computer 12C, among others (e.g., notebook, notepad, personal digital assistant, pager, Internet of things (IoT) devices (e.g., appliances, automotive devices, including autonomous vehicle device, etc.)). Note that in some embodiments, user devices 12 may include medical devices (e.g., as used at home or in a medical or research facility), including (wearable and non-wearable) devices associated with MRI imaging, CT scans, among other devices to acquire user data. The smartphone 12A may be in communications with the wearable device 12B and/or one or more computing devices 18 of the network 16. The smartphone 12A may include sensing functionality, including motion (e.g., acceleration), photoplethysmography (PPG), and/or electrocardiography (ECG) sensing. In one embodiment, the smartphone 12A comprises heart and/or breathing rate monitoring using a Philips Vital Signs Camera, or similar functioning devices from other manufacturers, to remotely measure heart and/or breathing rates using a standard, infrared (IR) based camera by sensing changes in skin color and body movement (e.g., chest movement), among others. ECG measurements may be achieved using electrodes disposed on, for instance, the casing of the smartphone 12A. In some embodiments, the smartphone 12A comprises an accelerometer, gyroscope, and location sensing functionality including a global navigation satellite system (GNSS) receiver (e.g., a global positioning system (GPS) receiver), which tracks and provides location coordinates (e.g., latitude, longitude, altitude) for the device 12A. The smartphone 12A may further include one or more interfaces for providing feedback of a monitored condition and/or activity, including a display screen (e.g., touch-type) to provide health data monitored, or accessed by, the smartphone 12A. The smartphone 12A comprises wireless/cellular communication functionality, including cellular, streaming and/or broadband (e.g., 3G, 4G, 5G, LoRa, etc.), Wi-Fi, Blue-tooth, NFC, etc., which may be used for the communication of sensing data (e.g., health data) and/or feedback information among the devices 12 and/or the computing devices 18 of the network 16.

The wearable device 12B is typically worn by the user (e.g., around the wrist or torso, as a patch, or attached to an article of clothing, or even embedded within a user), and comprises a plurality of sensors that track motion and/or physical activity of the user (e.g., steps, swim strokes, pedaling strokes, limb movement, etc.), activity type (walking, cycling, running, etc.) and is further configured to sense/measure or derive physiological parameters (e.g., heart rate, average heart rate, resting heart rate, inter-beat intervals, blood pressure, pulse rate, respiration, skin temperature, etc.) based on the sensor data, and optionally sense various other parameters (e.g., context, including outdoor temperature, humidity, location, etc.) pertaining to the surrounding environment of the wearable device 12B. In one embodiment, the wearable device 12B comprises an ECG sensor and a PPG sensor and an accelerometer and/or gyroscope. In some embodiments, the wearable device 12B may comprise a GNSS receiver, including a GPS receiver, which tracks and provides location coordinates (e.g., latitude, longitude, altitude) for the device 12B.

Data collected by the one or more sensors of the wearable device 12B may be communicated to the user via an interface (e.g., an integrated display) on the wearable device 12B. In one embodiment, the wearable device 12B uses the integrated display to also provide feedback to the user of a monitored condition and/or activity (e.g., health data). Such data collected by the wearable device 12B may be communicated to the smartphone 12A, the laptop 12C, and/or to other devices coupled to the network 16. Communication functionality of the wearable device 12B includes wireless functionality (e.g., near field communications (NFC), Blue-tooth, 802.11-based technology, streaming technology, including LoRa, and/or broadband technology including 3G, 4G, 5G, etc.) and/or wired functionality (e.g., via universal serial bus (USB), etc.).

The laptop 12C comprises typical data processing functionality, and communication functionality includes wireless communications (e.g., NFC, Blue-tooth, 802.11-based technology, streaming technology, including LoRa, and/or broadband technology including 3G, 4G, 5G, etc.) and wired functionality (e.g., USB, Ethernet, etc.) to receive/transmit (e.g., from/to the network 16 and/or the device 12B) health data.

One or more of the user devices 12 may include middleware (e.g., web services interfaces or web application programming interfaces (APIs) (e.g., SOAP, HTTP, XML, etc.), other APIs, etc.) that enable access to remote computing devices (e.g., to access electronic health records, personal health records, and/or other health data). For instance, cooperation between the user devices 12 and devices of the network 16 may be facilitated (or enabled) through the use of one or more APIs that may define one or more parameters that are passed between a calling application and other software code such as an operating system, library routine, function that provides a service, that provides data, or that performs an operation or a computation. The API may be implemented as one or more calls in program code that send or receive one or more parameters through a parameter list or other structure based on a call convention defined in an API specification document. A parameter may be a constant, a key, a data structure, an object, an object class, a variable, a data type, a pointer, an array, a list, or another call. API calls and parameters may be implemented in any programming language. The programming language may define the vocabulary and calling convention that a programmer employs to access functions supporting the API. In some implementations, an API call may report to an application the capabilities of a device running the application, including input capability, output capability, processing capability, power capability, and communications capability.

The wireless/cellular network 14 may include the necessary infrastructure to enable wireless and/or cellular communications between the user devices 12 and one or more devices of the network 16. There area number of different digital cellular technologies suitable for use in the wireless/cellular network 14, including: 3G, 4G, 5G, Global System for Mobile Communications (GSM), General Packet Radio Service (GPRS), CDMAOne, CDMA2000, Evolution-Data Optimized (EV-D0), EDGE, Universal Mobile Telecommunications System (UMTS), Digital Enhanced Cordless Telecommunications (DECT), Digital AMPS (IS-136/TDMA), and Integrated Digital Enhanced Network (iDEN), among others, as well as Wireless-Fidelity (Wi-Fi), 802.11, streaming, for some example wireless technologies.

The network 16 is depicted as a peer-to-peer (decentralized), blockchain or generally, distributed ledger network, though it should be appreciated that the network 16 may comprise additional and/or other types of networks in some embodiments. In general, a blockchain network comprises a system of data structures (e.g., databases) with properties of immutability and transparency. In one embodiment, the computing devices 18 or nodes record, share and synchronize data movement/data processing in their respective electronic ledgers (LDGRS), rather than keeping data centralized as in a traditional ledger. In general, distributed ledgers are the building blocks of "internet of value," and enable recording of data sharing and data sharing processing, including removal of patient data from a group, validation of removal, denial of access, removal of fields, etc.), without a need for a centrally coordinating entity or trusted $3^{rd}$ party. In one embodiment, each of the computing devices 18 may correspond to a respective healthcare provider possessing electronic health records for their patients. A distributed ledger organizes timestamped data/data share processing events into blocks, which are chained together in an append only mode. The creator of a block is decided upon using a distributed consensus algorithm. There are different kinds of consensus algorithms, with their aim to order the transactions in the block. The ledger may be public or private or some combination thereof, which in turn dictates the manner in which the distributed consensus is applied. For example, in a public/permissionless system where any party can write to the ledger, a Proof-of-Work (PoW) technique may be used. Proof-of-Stake (PoS) is another consensus approach which may be used in a permissionless distributed ledger context for reaching consensus. In this case PoS involves each participant taking a financial stake in the system in order to have the authority to write transactions. One aim of all of these distributed consensus algorithms is to implement some level of Byzantine Fault Tolerance (BFT), where the system is capable of reaching consensus even when there are some faulty or bad actors in the system. In some embodiments, the healthcare providers associated with the computing devices 18 may wish to maintain confidential transactions and checks of such transactions between each other, in which case a distributed ledger can maintain different ledgers configured to only be accessed by those authorized to access it.

In one embodiment, the network 16 provides a blockchain for trusted logging of data sharing sharing/processing events for all network stakeholders (e.g., healthcare providers, including third party providers). In one embodiment, data sharing/processing is published to the network 16 (e.g., via a write to the distributed ledger). That is, the computing devices 18 maintain a distributed ledger, which may include one or more of a log of previously executed data sharing/processing, etc., and which entity or entities (e.g., healthcare provider(s)) are linked to a given event (e.g., data sharing/processing, etc.). The distributed ledger records the data sharing/processing at or between the healthcare providers with respective timestamps generated when the data sharing/processing event takes place (e.g., removing data, sharing data, rejecting requests, denial of access, etc.).

In some embodiments, the network 16 may comprise a system of other types of data structures (e.g., other than a blockchain). The computing devices 18 may be embodied as application servers and/or data storage, which may collectively serve as a cloud computing environment (or other server network) for the user devices 12, performing processing and/or data storage on behalf of (or in some embodiments, in addition to) the user devices 12. When embodied as a cloud service or services, the computing devices 18 may comprise an internal cloud, an external cloud, a private cloud, or a public cloud (e.g., commercial cloud). For instance, a private cloud may be implemented using a variety of cloud systems including, for example, Eucalyptus Systems, VMWare vSphere®, or Microsoft® HyperV. A public cloud may include, for example, Amazon EC2®, Amazon Web Services®, Terremark®, Savvis®, or GoGrid®. Cloud-computing resources provided by these clouds may include, for example, storage resources (e.g., Storage Area Network (SAN), Network File System (NFS), and Amazon S3®), network resources (e.g., firewall, load-balancer, and proxy server), internal private resources, external private resources, secure public resources, infrastructure-as-a-services (IaaSs), platform-as-a-services (PaaSs), or software-as-a-services (SaaSs). The cloud architecture of the computing devices 18 may be embodied according to one of a plurality of different configurations. For instance, if configured according to MICROSOFT AZURE™, roles are provided, which are discrete scalable components built with managed code. Worker roles are for generalized development, and may perform background processing for a web role. Web roles provide a web server and listen for and respond to web requests via an HTTP (hypertext transfer protocol) or HTTPS (HTTP secure) endpoint. VM roles are instantiated according to tenant defined configurations (e.g., resources, guest operating system). Operating system and VM updates are managed by the cloud. A web role and a worker role run in a VM role, which is a virtual machine under the control of the tenant. Storage and SQL services are available to be used by the roles. As with other clouds, the hardware and software environment or platform, including scaling, load balancing, etc., are handled by the cloud.

In some embodiments, the computing devices 18 may be configured as multiple, logically-grouped servers (run on server devices), referred to as a server farm. The computing devices 18 may be geographically dispersed, administered as a single entity, or distributed among a plurality of server farms, executing one or more applications on behalf of, or processing data from, one or more of the user devices 12. The computing devices 18 within each farm may be heterogeneous. One or more of the computing devices 18 may operate according to one type of operating system platform (e.g., WINDOWS NT, manufactured by Microsoft Corp. of Redmond, Wash.), while one or more of the computing devices 18 may operate according to another type of operating system platform (e.g., Unix or Linux). The computing devices 18 may be logically grouped as a farm that may be interconnected using a wide-area network (WAN) connection or medium-area network (MAN) connection. The computing devices 18 may each be referred to as, and operate according to, a file server device, application server device, web server device, proxy server device, or gateway server device.

Figure 2:
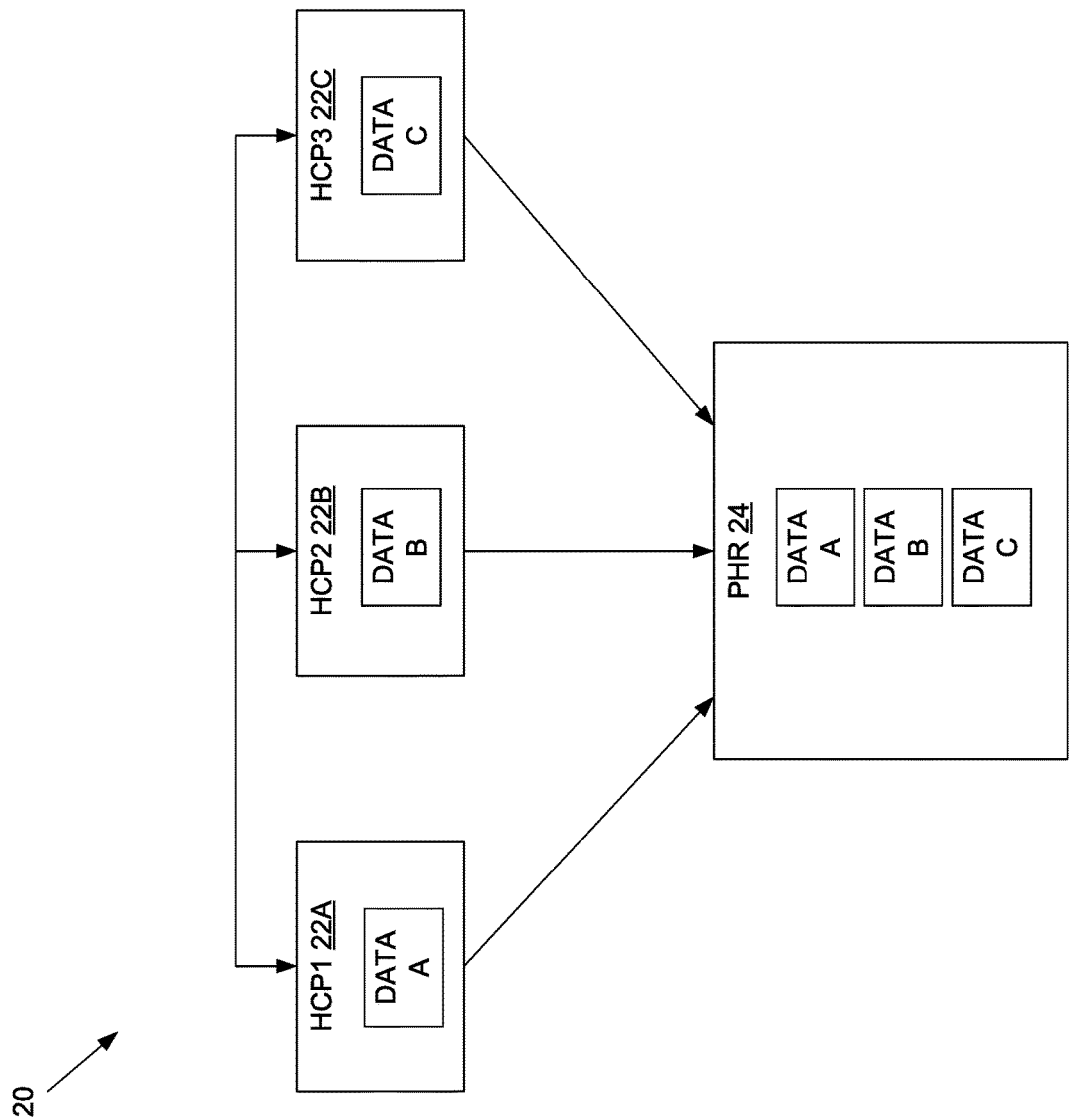
FIG. 2 is a schematic diagram that conceptually illustrates an example data privacy sharing system, in accordance with an embodiment of the invention.

Attention is now directed to FIG. 2, which conceptually illustrates an embodiment of an example data privacy sharing system 20. It should be appreciated by one having ordinary skill in the art that the data privacy sharing system 20 is merely a general illustration of one example, and that variations to the depicted arrangement and/or quantity of entities may be implemented and are contemplated to be within the scope of the disclosure. The data privacy sharing system 20 comprises plural healthcare providers (HCPs) 22, including HCP1 22A, HCP2 22B, and HCP3 22C. Each healthcare provider 22 may include one or more of the computing devices 18 (FIG. 1). Each healthcare provider 22 maintains a record of their patients, including data A maintained by HCP1 22A, data B maintained by HCP2 22B, and data C maintained by HCP3 22C. In one embodiment, the data may comprise electronic health records, which may include (private) information about their health and/or treatment while at the respective facility, including information about their allergies, adverse drug reactions, family medical history, any chronic diseases, illnesses and hospitalizations, lab results, imaging reports (e.g. X-Rays, CT scans etc.), prescription records, medications and dosages, vaccinations, surgeries, etc. In some embodiments, this data (data A, B, and C) may be communicated to a user's personal health record (PHR) 24. In one embodiment, the PHR 24 may be maintained as part of a third party service. The data A, B, C associated with each respective healthcare provider 22A, 22B, and 22C is accessible to each of the healthcare providers 22 based on meeting certain criteria for sharing. In other words, data A maintained (e.g., stored) by HCP1 is accessible by HCP2 (and/or HCP3), assuming the appropriate criteria are met per the methods described in FIGS. 3A-3B below. That is, certain embodiments of a data privacy sharing system 20 enable the sharing of the patient data according to any one of plural methods based on various criteria as set forth in the explanation below, the criteria based on one or more characteristics of the user data.

Figure 3A:
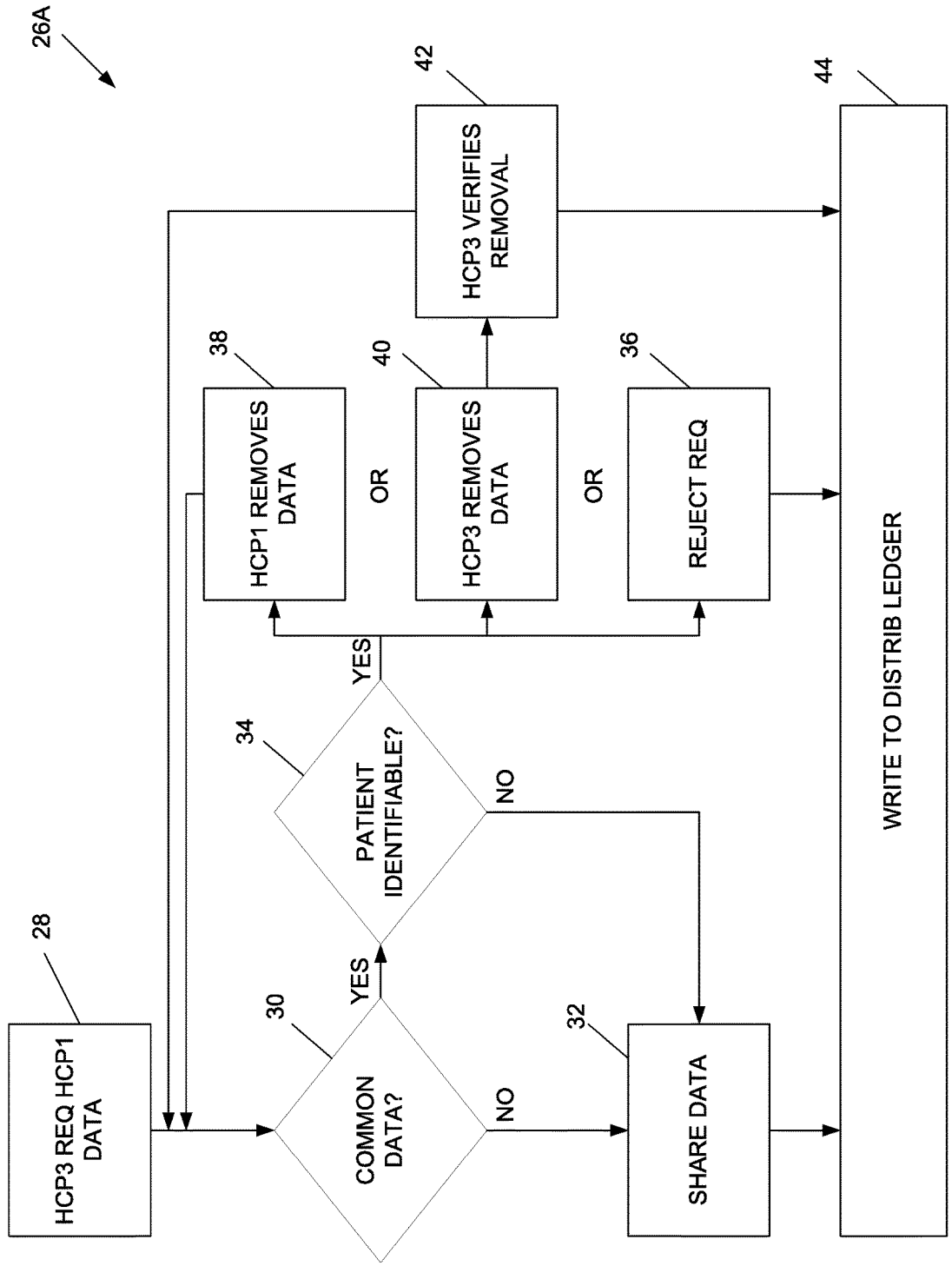
FIGS. 3A-3B are flow diagrams that illustrate example methods for sharing data between healthcare providers while preserving data privacy, in accordance with an embodiment of the invention.
Figure 3B:
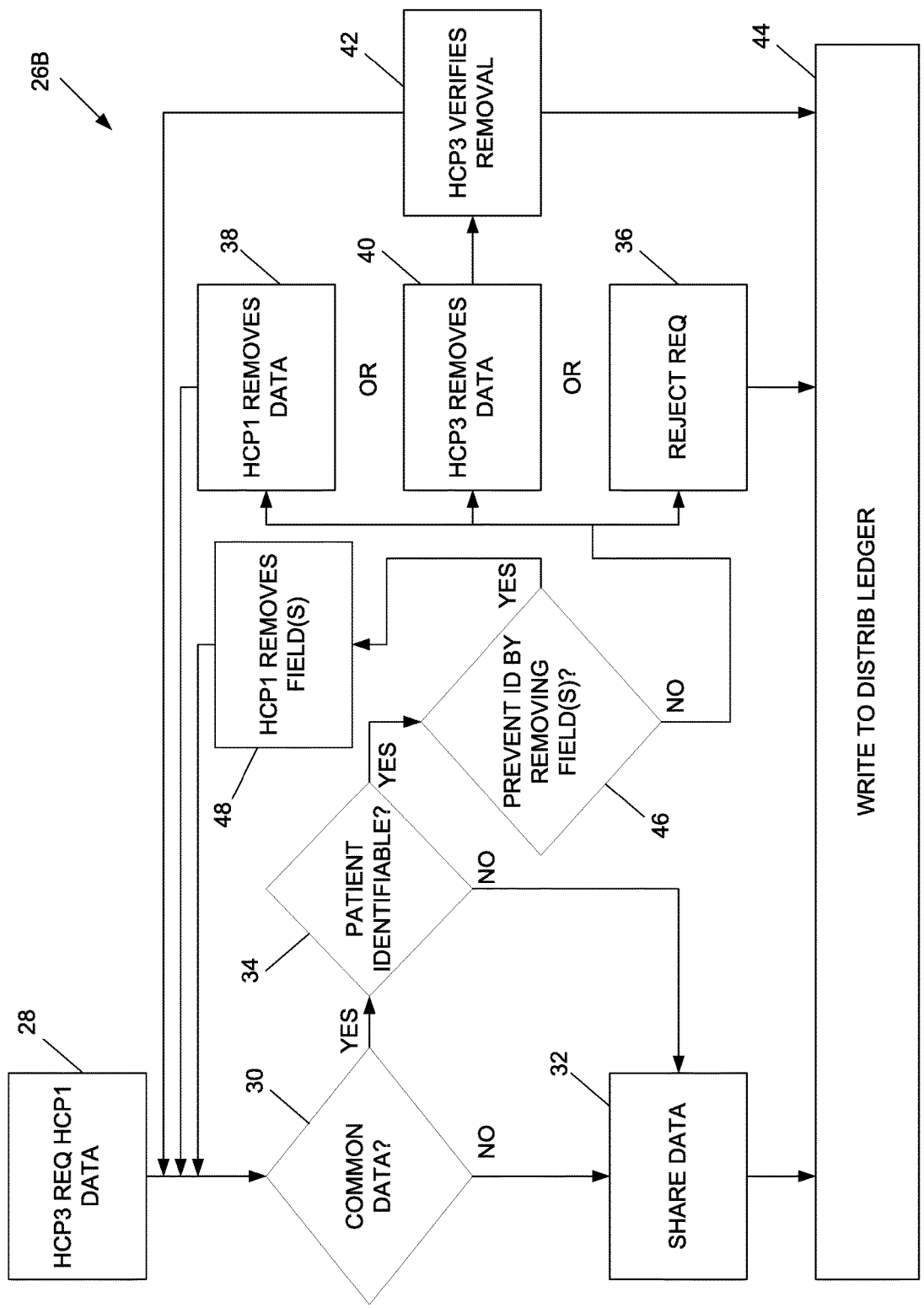

FIGS. 3A-3B are flow diagrams that illustrate example methods 26 (e.g., 26A, 26B) for sharing data between healthcare providers while preserving data privacy. For instance, and referring to FIG. 3A, a method 26A is depicted that an embodiment of the data privacy sharing system 20 may use to enable the sharing of data using a protocol, or stated otherwise, plural criteria based on one or more characteristics of the user data accessible by the respective entities (e.g., HCP1, HCP3). In one embodiment, the criteria is established by one or any combination of the healthcare providers, government/government regulations (e.g., new general data protection regulations or GDPR in Europe), the user (e.g., patient, such as via user consent), or any other third party. In other words, it is presumed that the apparatus and another computing device (e.g., HCP1 and/or HCP3) are aware of any user consent and/or government driven restrictions in establishing the criteria. The method 26A may be implemented by one or a combination of computing devices 18 with or without human intervention. For instance, in some embodiments, operators may be involved in a minor way to ensure quality control, integrity, and/or to check transactions (e.g., via logs stored in the blockchain). In (28), a healthcare provider (e.g., HCP3) requests data from another healthcare provider (e.g., HCP1). As indicated above, reference to HCPs performing various functionality is understood to refer to a respective computing device 18 performing the respective function. In view of privacy regulations it is assumed that upon such a request (or in some cases, preliminary to the request or both preliminary to, and subsequent to, the request in some cases), there will be communication and agreement between both parties (e.g., via computing devices 18) to ensure that only relevant, and therefore, a minimal set of data, is shared. This agreement may contemplate governmental regulations and/or patient requirements. The sharing of minimal data may be ensured by HCP1 requesting that HCP3 verify why HCP3 needs certain type of data, and by HCP1 making sure that only relevant parts of data are shared. For instance, assuming that HCP3 requests data on all health failure patients for a study of heart modelling, HCP1 removes all information that is not directly relevant to the request, such as information about a broken leg as one illustrative example. Since data sharing based on data regulations are known to those having ordinary skill in the art, and varied depending on the location/region of use, further description of the same is omitted here for brevity. It is further assumed that both HCP1 and HPC3, when sharing data per established criteria, submit already anonymized data to each other. HPC3, for example, may reject data reception if data from HCP1 is not anonymized.

In (30), a decision engine (e.g., of a computing device 18) determines a chance/risk/probability of (presence of, though in some embodiments, may look to absence of) common patients among the data sets of HCP1 and HCP3. That is, the determination is based on a likelihood function (e.g., with a computed value ranging between no presence [0] and certainty of presence [1], or values/logic indicating low likelihood, reasonable likelihood, high likelihood, etc., among other probability or risk measures). In one embodiment, this decision engine may be run by a third party trusted by both HCP1 and HCP3, in a distributed ledger where both HCP1 and HCP3 store their data or some information about their data, or elsewhere in the computing device 18. If there is a trusted third party, or a regulation body, both healthcare providers HCP1 and HCP3 may submit their (anonymized) data, and the third party decision engine decides if there is any (e.g., reasonable, sufficient) risk of common patients. Instead of using a trusted third party, which may have its own limitations as discussed above, in some embodiments, a multi-party computation method may be implemented. In this case, the computation to check if there may be any common patients is shared between HCP1 and HCP3. In a multi-party computation, a given number of participants, such as HCP1, HCP2, HCP3, etc., each have private data, that is, private data1, private data2, private dataN, respectively. A value of a public function is computed on the private data: F(private data1, private data2, . . . , private dataN) while keeping the contributor's inputs secret. In one embodiment, a multi-party computation comprises a garbled circuit. A garbled circuit comprises a cryptographic protocol that enables two-party secure computation in which two mistrusting parties may jointly evaluate a function over their private inputs without the presence of a trusted third party. In the garbled circuit protocol, the function is described as a Boolean circuit.

In some embodiments, the checks may be performed in a trusted execution environment (TEE), which uses trusted code and trusted hardware, where both parties submit their data and processing occurs. A trusted execution environment comprises a secure area of a main processor and guarantees code and data loaded inside is protected with respect to confidentiality and integrity. A trusted execution environment as an isolated execution environment provides security features, including isolated execution, integrity of applications executing with the trusted execution environment, along with confidentiality of their assets. In general terms, the trusted execution environment includes an execution space that provides a higher level of security than a rich mobile operating system and more functionality than a secure element. For instance, the trusted execution environment comprises an isolated environment that runs in parallel with the operating system, providing security for the rich environment. It is intended to be more secure than the User-facing OS (which GlobalPlatform calls the REE or Rich Execution Environment) and offers a higher level of performance and functionality than a Secure Element (SE), using a hybrid approach that utilizes both hardware and software to protect data, thus providing a level of security sufficient for many applications. Trusted applications running in a trusted execution environment have access to the full power of a device's main processor and memory, while hardware isolation protects these from user installed apps running in a main operating system. Software and cryptographic isolation inside the trusted execution environment protect the trusted applications contained within from each other. In one embodiment, the trusted execution environment is run on a computing device 18 associated with a requesting (data share requesting) healthcare provider (e.g., HCP3), a computing device 18 associated with a recipient of the request (e.g., HCP1), a third party computing device 18, or any combination thereof.

In one embodiment, the output of the decision engine is binary (e.g., "YES", there are (presence of) common patients, or "NO", there are no (presence of) common patients, as depicted in FIG. 3A). In some embodiments, the output of the decision engine comprises a fuzzy variable (e.g., a number between 0 and 1, where 0 equates to no common patients and 1 equates to common patients) that indicates a risk/likelihood/probability of having common patients. The fuzzy variable may be based on a fuzzy function using a likelihood function, wherein the fuzzy function and/or likelihood function is pre-set or adaptive. In the fuzzy case, a threshold or other function may be specified, and if the fuzzy variable is lower than a threshold (e.g., thr=0.5), the determination is that there are no common patients or, that the chance/risk/probability of common patients is lower, and therefore may be deemed as sufficient to enable sharing of data in view of the data sharing regulations established by one or any combination of the healthcare providers, governing bodies, or data characteristics, etc. The use of a fuzzy decision output contemplates that the data available to the third party, multi-party computation, or trusted execution environment that makes the decision, or data in the ledger, may represent only a segment of the whole data sets in HCP1 and/or HCP2, and therefore may not permit a decision with full certainty. For example, if the information available to the third party is that HCP1 contains data from Manufacturer A employees and HCP2 contains data from people living in a region where Manufacturer A is known to be the largest employer, the decision engine may indicate that there is a high risk that the two data sets intersect and contain the same patient (and hence additional criteria needs to be addressed). In other words, the criteria is based on one or more characteristics (e.g., regional data of employees) of the user data sets.

As explained above, the decision engine output may be binary. In one embodiment, it is assumed that all patients have an anonymous identifier (e.g., a (national) patient ID number). In some embodiments, such as when blockchain processing is used, keys generated during the blockchain process may be used to generate unique identifiers. Using the ID number, the decision engine may also know that the patients are common (through the common anonymous identifier)—just not who they are (and of course, cannot obtain their identity just from the ID number). For instance, HCP1 and HPC3 may share the common patient identifier (ID number) with, for instance, a trusted third party. In this case, the decision output of (30) is binary (e.g., a definite or absolute YES or NO).

Referring again to the method 26, if there are no common patients ("NO" to (30)), or if the risk of having a common patient is below a set threshold (or satisfies or fails to satisfy another type of function), then the data sharing is allowed (32). Otherwise ("YES" to (30)), further privacy ensuring checks are performed (e.g., additional criteria are addressed to determine whether data sharing/access is allowed) as explained below.

In (34), a decision engine determines if the patient can be identified or not. The description above for (30) is applicable to (34) in the sense that the decision may be binary (e.g., YES or NO) or fuzzy (e.g., between 0 and 1, and then using a function that takes the fuzzy output as one of its inputs (e.g., a threshold), the path can be determined.) The decision engine may be the same as that for (30), or an additional decision engine. In some embodiments, the decision engine may be operated by a third party, or in another computing device 18 based on multi party computation, or run in a trusted execution environment, where HCP1 and HCP3 share their anonymized data.

In some embodiments, (30) and (34) may be combined and/or operated as a single decision engine. In some embodiments, to optimize resource usage and/or to speed up computations, (30) and (34) may be implemented as separate decision engines.

In some embodiments, a higher level representation of the data may be used. For example, one potential implementation for the decision engine(s) is a data driven approach (e.g., for use in derivation of rules or training machine-learning models), where data (e.g., data types) that may lead to the patient identification, when combined with each other, may be specified, and depending on the number of the availability of these data (types), a score, including a probabilistic score or risk score, may be calculated. For example, possible risk scores may be as follows: age=0.1; age+ gender=0.3; age+gender+location=0.5; age+gender+location+employer=0.7; age+gender+location+employer+salary=0.9. In one embodiment, the data driven approach comprises computation of a risk score as a function of weights for respective data in the first and second user data sets. In this example, it is illustrated that by having different data (e.g., different data types) combined with each other, the risk of identification increases. In other words, if data from HCP1 and HCP3 contains only the age, then the risk is estimated to be low, but if both data sets contain age, gender, and location, then the risk increases. If a patient cannot ("NO" in (34)) be identified (e.g., with a sufficient probability), then data is shared (32), otherwise different options are possible.

Some examples of methods involved in determining a risk of common patients are described below. For instance, based on descriptive features or characteristics of the data sets (where these descriptive features may be public information in some embodiments), with every new description, or feature available, the risk score may be updated. The descriptive features can be presented at once, or based on the risk score estimated from the previous step. For example, a computation may involve determining for Feature1 the minimum age of people in the data sets, where set1=30, set2=50, and based on this determination, the next feature can be determined. Further, the decision making may further determine the percentage of people with age higher than, say, 50 years of age. The determination may be that set1=2%, and set2=100%. Accordingly, the decision engine estimates that there is a 2% risk of intersection. Some descriptors may be more informative than the others. For example, knowing the location, employer, etc. of the users may be associated with the risk of having the same people in the two sets.

In some embodiments, prior information may be more relevant for decision engine computations. For example, knowledge that previously collected datasets are intersecting may be used for computations. It is likely, for example, that studies conducted from the same research lab have subjects that participated in multiple studies, and in many cases, this is also reported in publications.

In some embodiments, another method used by the decision engine can be based on analysis of a sub-set of whole data sets. Randomly representative samples from each data set (which may be publically available or anonymized) may be used to compute the probability of intersection for two data sets. For instance, assuming 10 subsets for cohort1, and 10 subsets for cohort2, the decision engine can calculate the risk score using the data available for the subset pairs, and use it to compute a risk score for the cohorts.

In some embodiments, another method used by the decision engine may be based on a mathematical function, or computation, that uses the data in the sets and outputs a value, or range of values. Based on these values, it can be computed if there may be intersection. In this case, each of HCP1 and HCP3 can evaluate the function without disclosing the inputs to the function.

If the decision engine estimates (e.g., with a certain probability) that a patient can be identified ("YES" to (34)), several options are possible (options separated by "OR" in FIG. 3A). One option is that HCP1 can reject the data sharing (reject request) (36). Alternatively, the HCP1 can be informed by the decision engine (at (34)) which patient is potentially identifiable, and it can remove the data for the patient before sharing with HCP3 (38). Alternatively, the HCP3 can be asked to remove their data of the patients with a high risk of unintentional identification (40), and to verify the removal of the data to HCP1 (42). The verification can happen through a trusted third party, or by creating a record in the ledger. In one embodiment, where all the transactions are stored in a distributed ledger (44), all actions are traceable and therefore all parties may be liable or accountable in case of misinformation, or non-cooperation. For example, if HCP3 does not delete the data (in (40)), while it claims (e.g., indicates) to have done so, this can be discovered by inspecting the data in HCP3 and the transaction written to the ledger. Note that the method 26A (and similarly for method 26B as described below) may be performed without the involvement of human operators (e.g., automatically or autonomously), though in some embodiments, human intervention is permitted at one or more of the steps. For instance, human involvement may be based on data features or characteristics (e.g., in the case of very sensitive data, human intervention may be a defined requirement, or in some cases, human involvement may depend on the value of a fuzzy variable). In other words, in some embodiments, human involvement in the method 26 (e.g., 26A, 26B) depends on the type/feature of the shared data and/or on the output of the decision engine involved in the processing of binary or fuzzy outputs. In some embodiments, a human operator may be involved if there is an audit (e.g., a formal, systematic and independent examination of the records/documents).

FIG. 3B is another embodiment that is similar to the method 26A of FIG. 3A, with the addition that the decision engine corresponding to (34) informs HCP1 (and/or HCP3) which field of data are leading to the identification of the patient, and instead of rejecting to share the whole set of data belonging to the patient, HCP1 (and/or HCP3, or a third party) can decide whether to remove only the fields that risk identification (46). If so ("YES" to (46)), HCP1 (or HCP3, or a third party) removes the field(s) (48), otherwise ("NO" to (46)), one of the other options is performed (36, 38, or 40) as described above. Note that verification may be performed by HCP1 or HCP3 (or a third party).

Note that variations to the above methods 26A and 26B are contemplated and implemented in some embodiments. For instance, one alternative to deletion of data (or data field), or to rejection of sharing of data, may be that HCP1 agrees to share the data, but in processed manner. In other words, based on the evaluation of whether there may be common or identifiable users (e.g., as a function of likelihood of presence or identification), HCP1 may decide to process (e.g. encode, or analyze) the data based on the input from HCP3. For example, if it is communicated that HCP3 is requesting the data in order to compute the treatment costs for people with high blood pressure, and if HCP1 is not willing to share all data, then HCP1 can process the data and only share the information requested by the HCP3. Related to this, in some embodiments, HCP1 may agree to share the data together with a processing function, and HCP1 may impose a restriction that the data is first processed using the supplied function before any other processing.

It is noted that FIGS. 3A-3B describe methods 26A and 26B where there is an emphasis on how to determine data sharing based on criteria involving user commonality and then user identification. In other words, the methods 26A and 26B describe criteria based sharing, where the criteria has been established (e.g., negotiated and agreed upon) by one or any combination of the healthcare providers (e.g., HCP1 and HCP3) and governing bodies/regulations and evaluated prior to data sharing. In some embodiments, the criteria comprises set rules based criteria (e.g., pre-set or pre-determined). In some embodiments, the criteria may comprise fuzzy rules based criteria, which is determined based on the characteristics of the data available in, say, HCP3 and data requested by HCP1. In some embodiments, access determinations may be based on a fuzzy function using a likelihood function, where the fuzzy function or likelihood function is either preset or adaptive. Accordingly, though determining if there is commonality and/or identifiability of patients among user data sets is one feature of certain embodiments of a data sharing system, in some embodiments, other features may be realized, including, say, preventing HCP3 from discovering, from the shared data, secret information about HCP1. More generally, though commonality via presence is described as one criteria, certain embodiments of a data sharing system may determine access based on criteria that is based on one or more characteristics of the user data sets. For instance, the criteria may be based on the likelihood of a cancer patient, or a patient below a certain age, or where the data is collected.

Note that with user consent/permissions and criteria established by the user, different users may have different privacy requirements. For instance, some users may have signed consent forms that are recorded and enable data to be shared even if identification is possible, whereas some users may have declined the sharing of data even in the case of no-identification. In some embodiments, privacy requirements may fall somewhere in between these two requirements/options. In some embodiments, user data privacy regulations depend on the type of data (e.g., sharing permitted only when the data is of a certain type).

Figure 4:
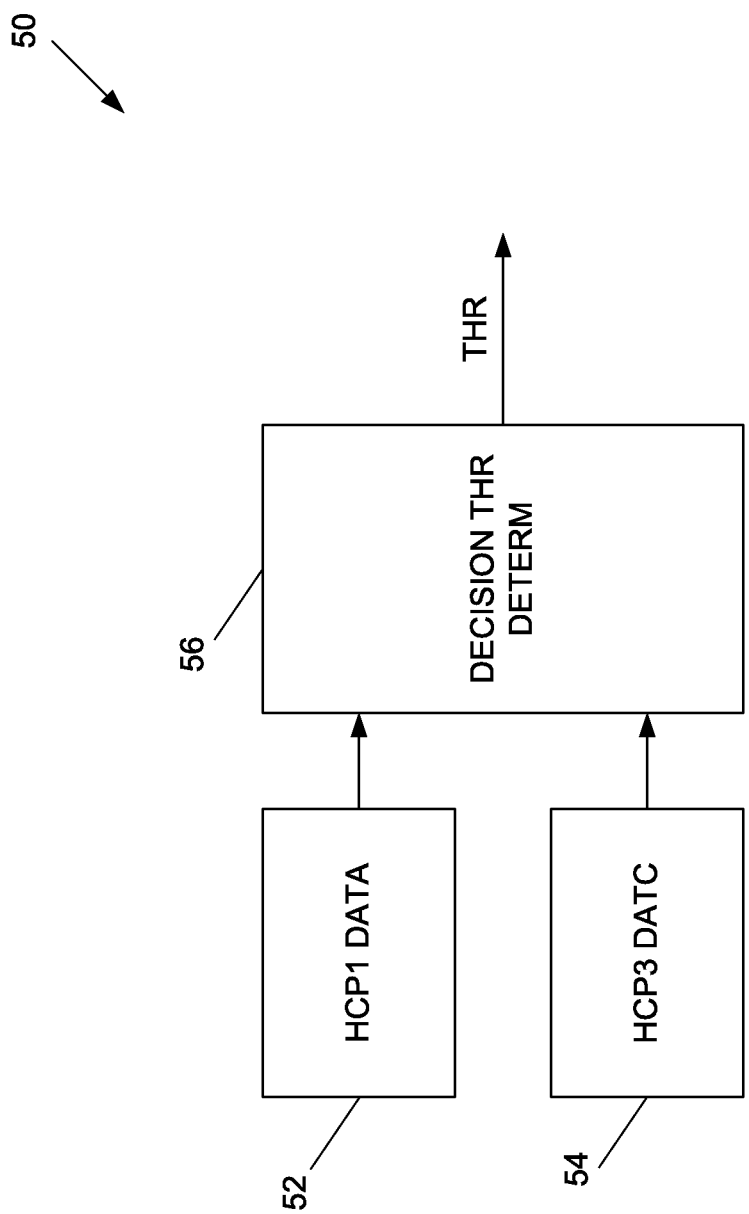
FIG. 4 is a schematic diagram that illustrates an example method for determining whether there is a threshold level of commonality of patient data among healthcare provider data, in accordance with an embodiment of the invention.

In FIGS. 3A-3B, the decision engine determination of common data (30) may be based on a pre-set threshold (e.g., as one type of function). In some embodiments, the threshold may be adaptive. FIG. 4 conceptually illustrates an embodiment where an adaptive threshold is used in (30). In particular, with regard to (30) of FIG. 3A or 3B, an adaptive setting of the threshold may be performed based on data characteristics and/or healthcare provider characteristics. The HCP1 data 52 and HCP3 data 54 is inputted to the decision engine 56. In other words, the decision engine 56 determines the threshold based on the data 52, 54 to be shared, as well as characteristics of the healthcare providers (HCP1 and HCP3) sharing the data. For example, if data to be shared includes non-sensitive information (as determined by the patient, or a third party including internal HCP regulations and/or global/country regulations), then the threshold may be set higher (increasing the probability that fuzzy risk variable will be lower than the threshold, and therefore increasing the chance of data sharing). On the other hand, if the data is highly sensitive (as determined by the patient and/or third party regulations), then the threshold may be set to a lower value (ensuring higher accuracy, or higher sensitivity for the decisions in 30 and 34 (FIGS. 3A-3B). In addition to the data characteristics, the trust between HCP1 and HCP3, which are going to share the data, may be taken into account. If parties trust each other, the threshold can be set higher, and if they do not trust each other, the threshold can be lower.

Though an adaptive threshold is described in conjunction with FIGS. 3A-4 as one example, other functions may be used in some embodiments. That is, referring to the thresholding example described above, as a result of (30) and (34) of FIGS. 3A-3B, outputs comprise likelihood of having common data, or identifiable data, respectively. The threshold is then compared to the computed likelihood to decide on what action to take. As described, in the text in case of sensitive data, the threshold may be set to minimize risk. In a sense, the decision of common data is based on the likelihoods and the thresholds that are calculated. Thresholding in this case is one of the final steps. In some embodiments, a function is applied (e.g., the function being a finite element model, or machine learning driven, or both) that calculates likelihoods as a result of (30) and (34). Based on the calculated likelihood, a decision is made if data is common, or identifiable. Generally, classification algorithms first calculate the likelihood and then use this to compute final result. In other words, for (30) and (34), there are many implementations that are possible. Note that using classification algorithms may be implemented in some embodiments, though in some embodiments, classification may not be implemented. For instance, once acquiring data of a given type, that data itself may be used to compute the likelihoods. In one embodiment, machine learning, either in supervised or unsupervised manner, may be applied. When supervised, a human can be involved in defining categories, or specific clusters, or specific parameters, and features. When unsupervised, the classification happens without human involvement. For classification, or clustering, there are many different candidate machine learning algorithms that can be used, including K-mean, N-nearest neighbors: the intercluster and intra-cluster variability can be used to compute likelihoods and correspondingly the risk of common data. Decision trees, random forest, Gaussian mixture models, support vector machines, logistic regression, linear regression, neural networks, convolutional neural networks, are some of the other classification functions that may be used in some embodiments.

Figure 5:
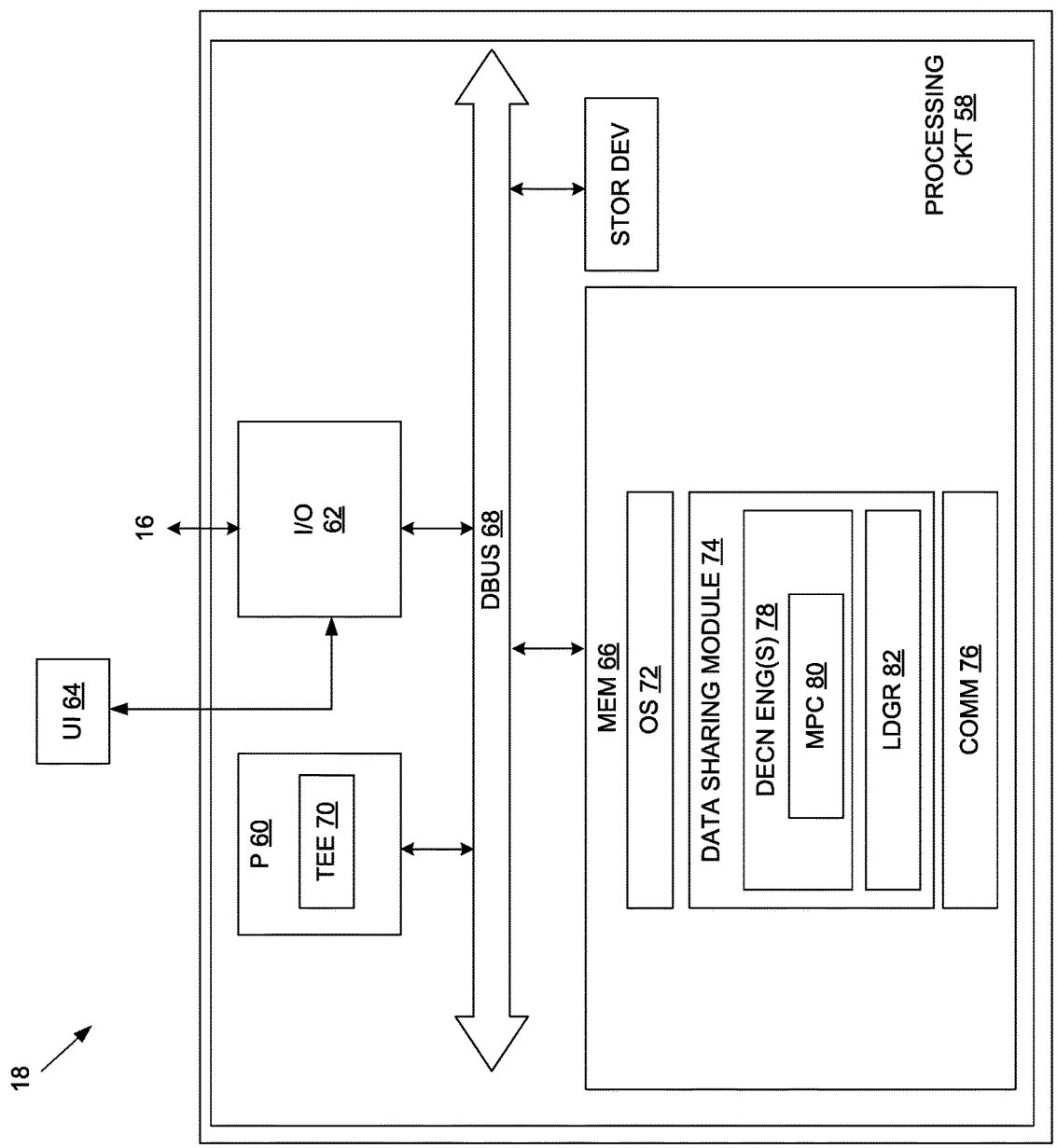
FIG. 5 is a block diagram that illustrates an example computing device that may implement, all or in part, one or more of the methods of FIGS. 3A-3B, in accordance with an embodiment of the invention.

Having described an embodiment of a data privacy sharing system 20 and associated methods 26A and 26B, attention is directed to FIG. 5, which illustrates an embodiment of an example computing device 18. The computing device 18 may be embodied as an application server, computer, among other computing devices. One having ordinary skill in the art should appreciate in the context of the present disclosure that the example computing device 18 is merely illustrative of one embodiment, and that some embodiments of computing devices may comprise fewer or additional components, and/or some of the functionality associated with the various components depicted in FIG. 5 may be combined, or further distributed among additional modules or computing devices, in some embodiments. The computing device 18 is depicted in this example as a computer, such as one providing a function of a node in a blockchain, peer-to-peer network 16, though similar applicability is understood for non-blockchain implementations. It should be appreciated that certain well-known components of computers are omitted here to avoid obfuscating relevant features of the computing device 18. In one embodiment, the computing device 18 comprises a processing circuit 58 (PROCESSING CKT) that comprises one or more processors (one shown), such as processor 60 (P), input/output (I/O) interface(s) 62 (I/O), one or more user interfaces (UI) 64, which may include one or more of a keyboard, mouse, microphone, speaker, etc., and memory 66 (MEM), all coupled to one or more data busses, such as data bus 68 (DBUS). In some embodiments, the user interfaces may be coupled directly to the data bus 68. In one embodiment, the processor 60 may include a trusted execution environment (TEE) 70, which comprises hardware and/or software in a secure area of the processor 60 configured to compare data sets to be shared between healthcare providers to determine whether there is a presence of a patient or patients common to both data sets, or determine whether there is a threshold risk/probability of such commonality (e.g., based on a likelihood function). In some embodiments, a separate, dedicated security processor may be used to implement the trusted execution environment. In some embodiments, the TEE 70 is further configured to determine if the common patient(s) can be identified, or determine a threshold (or other function-based) risk/probability of being identified. In some embodiments, the TEE 70 may use a pre-set threshold, or a variable threshold as set forth above. In some embodiments, the TEE 70 may be omitted.

The memory 66 may include any one or a combination of volatile memory elements (e.g., random-access memory RAM, such as DRAM, and SRAM, etc.) and nonvolatile memory elements (e.g., ROM, Flash, solid state, EPROM, EEPROM, hard drive, tape, CDROM, etc.). The memory 66 may store a native operating system, one or more native applications, emulation systems, or emulated applications for any of a variety of operating systems and/or emulated hardware platforms, emulated operating systems, etc. In some embodiments, a separate storage device (STOR DEV) may be coupled to the data bus 68 or as a network-connected device (or devices) via the I/O interfaces 62 and the network 16. The storage device may be embodied as persistent memory (e.g., optical, magnetic, and/or semiconductor memory and associated drives), and in some embodiments, may be used to store data depicted as stored in memory 66. In some embodiments, the memory 66 may be configured as a non-transitory, computer readable storage medium.

In the embodiment depicted in FIG. 5, the memory 66 comprises an operating system 72 (OS) and application software that includes a data sharing module 74 and a communications module (COMM) 76. The data sharing module 74 may include machine learning or rule-based algorithms, and may include one or more decision engines (DECN ENG(S)) 78, which in one embodiment comprises a multi-party computation module (MPC) 80. The data sharing module 74 also comprises a distributed ledger (LDGR) 82 in some embodiments (e.g., blockchain embodiments). For instance, distributed ledger 82 may include distributed ledger 44 (FIGS. 3A-3B). In some embodiments, functionality for the one or more of the aforementioned modules may be combined, such as running the decision engine(s) 78 in the distributed ledger 82. Note that the memory 66 may also be referred to herein as a non-transitory, computer readable storage medium. The data sharing module 74 comprises executable code or instructions that configure the processor 60 to perform the functionality described in association with FIGS. 3A-4. For instance, the decision engine(s) 78 (e.g., the multi-party computation module 80, which in one embodiment, may comprise a garbled circuit as described above, or as implemented in the distributed ledger 82) are configured to determine whether there is a patient or patients common to both data sets, or determine whether there is a threshold risk/probability of such commonality (or using other functions). In some embodiments, the decision engine(s) 78 are further configured to determine if the common patient(s) can be identified, or determine a threshold risk/probability (or using other functions) of being identified. In some embodiments, the decision engine(s) 78 may use a pre-set threshold, or a variable threshold as set forth above. Functionality of the data sharing module 74 further comprises identifying one or more fields that may enable identification of a patient(s), rejecting requests for sharing, denial of access, removing identifiable data, and verifying the removal of data. The data sharing module 74 (e.g., decision engine(s) 78) may implement a data driven approach, including for use in derivation of rules or training machine-learning models, where the data driven approach comprises computation of a risk score as a function of individual weights for respective data types in the first and second user data sets. The distributed ledger 82 records and time stamps the sharing of data, the rejection of sharing requests, and the verification of data removal. The communications module 76 operating in conjunction with the I/O interfaces 62 (collectively referred to as a communications interface) comprises functionality to communicate with the user devices 12 and/or other devices of the network 16, and may include connectivity logic for communications with an Ethereum network among other networks. For instance, the communications module 76 may be used to respond to data sharing requests (e.g., reject the data share request, instruct the computing device 18 of the requesting healthcare provider to delete data/field(s), validate data deletions, etc.).

Note that in some embodiments, functionality of the data sharing module 74 and/or trusted execution environment 70 may be implemented in one or more other computing devices 18, including computing device(s) associated with a trusted third party or computing device(s) associated with another healthcare provider, and communicated (e.g., at different steps of the method 26A, 26B, FIGS. 3A-3B) to the other computing device 18. For instance, said functionality may be implemented at HCP1 or HCP3 in FIGS. 3A-3B. In some embodiments, functionality of the data sharing module 74 and/or trusted execution environment 70 may be implemented in distributed fashion (e.g., using plural computing devices 18). For instance, and continuing the prior example, said functionality may be implemented in HCP1 and HCP3, or HCP1, HCP3, and a trusted third party device.

Execution of the data sharing module 74 (including associated components 78-82) and the communications module 76 may be implemented by the processor 60 under the management and/or control of the operating system 72. The processor 60 may be embodied as a custom-made or commercially available processor, a central processing unit (CPU) or an auxiliary processor among several processors, a semiconductor based microprocessor (in the form of a microchip), a macroprocessor, one or more application specific integrated circuits (ASICs), a plurality of suitably configured digital logic gates, and/or other well-known electrical configurations comprising discrete elements both individually and in various combinations to coordinate the overall operation of the computing device 18.

The I/O interfaces 62 comprise hardware and/or software to provide one or more interfaces to devices coupled to the network 16, as well as to other devices such as the user interface. In other words, the I/O interfaces 62 may comprise any number of interfaces for the input and output of signals (e.g., analog or digital data) for conveyance of information (e.g., data) over various networks and according to various protocols and/or standards. In some embodiments, data may be received over the network 16 based on input from speech-to-speech interfaces (e.g., Alexa), text-based interfaces (e.g., using natural language processing) and/or chatbots.

The user interfaces 64 may include a keyboard, mouse, microphone, immersive head set, etc., which enable input and/or output by an administrator or other user. In some embodiments, the user interfaces 64 may be configured as a speech-to-speech interface, text-based interface, and/or chatbot.

When certain embodiments of the computing device 18 are implemented at least in part with software (including firmware), as depicted in FIG. 5, it should be noted that the software (e.g., the data sharing module 74 and the communications module 76) can be stored on a variety of non-transitory computer-readable (storage) medium for use by, or in connection with, a variety of computer-related systems or methods. In the context of this document, a computer-readable storage medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the computing device 18 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), relays, contactors, etc.

Figure 6:
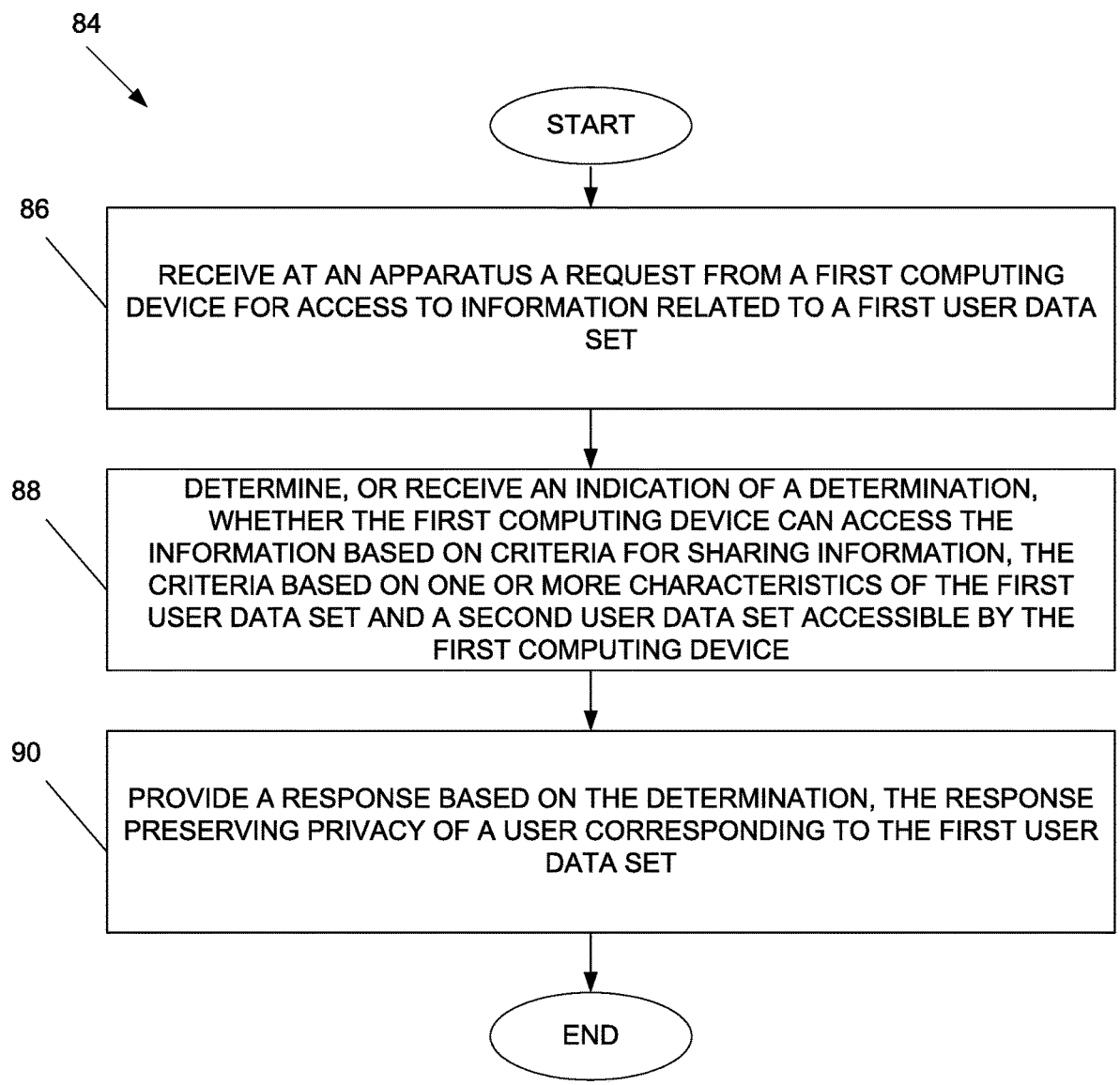
FIG. 6 is a flow diagram that illustrates an example method for sharing data between healthcare providers while preserving data privacy, in accordance with an embodiment of the invention.

Having described certain embodiments of a data privacy sharing system (e.g., data privacy sharing system 20, FIG. 2), it should be appreciated that one embodiment of an example method for sharing data between healthcare providers while preserving data privacy, depicted in FIG. 6 and denoted as method 84, which is shown bounded by a start and end, comprises receiving at an apparatus a request from a first computing device for access to information related to a first user data set (86); determining, or receiving an indication of a determination, whether the first computing device can access the information based on criteria for sharing information, the criteria based on one or more characteristics of the first user data set and a second user data set accessible by the first computing device (88); and providing a response based on the determination, the response preserving privacy of a user corresponding to the first user data set (90).

Any process descriptions or blocks in flow diagrams should be understood as representing modules, segments, or portions of code which include one or more executable instructions for implementing specific logical functions or steps in the process, and alternate implementations are included within the scope of the embodiments in which functions may be executed out of order from that shown or discussed, including substantially concurrently or in reverse order, depending on the functionality involved, as would be understood by those reasonably skilled in the art of the present disclosure. In some embodiments, one or more steps may be omitted, or further steps may be added.

In one embodiment, a system is disclosed comprising: an apparatus, comprising: a communications interface configured to enable communications with one or more computing devices; one or more processors configured by instructions to: receive a request from a first computing device for access to information related to a first user data set; determine, or receive an indication of a determination, whether the first computing device can access the information based on criteria for sharing information, the criteria based on one or more characteristics of the first user data set and a second user data set accessible by the first computing device; and provide a response based on the determination, the response preserving privacy of a user corresponding to the first user data set.

In one embodiment, the prior system, wherein the criteria is set rules based or fuzzy rules based.

In one embodiment, any one of the prior systems, wherein the criteria comprises adaptive criteria.

In one embodiment, any one of the prior systems, wherein the criteria comprises commonality of one or more users associated with the first user data set and the second user data set according to a first likelihood function, wherein the one or more processors are configured by the instructions to determine, or receive the indication of the determination, by: determining, alone or in combination with one or more other devices, or receiving an indication of a determination from the one or more other devices, whether according to the first likelihood function there is a presence of at least one common user among the first user data set and the second user data set, wherein the determination or receipt of the indication of the determination is based on computations performed on an anonymized version of the first and second user data sets.

In one embodiment, any one of the prior systems, wherein the at least one common user comprises a user identifier, wherein responsive to an absence of the user identifier in one of the first and second user data sets, the response comprises the one or more processors sharing an anonymized version of the first user data set with the first computing device.

In one embodiment, any one of the prior systems, wherein the response is based on the determination or receipt of the indication of the determination of the presence, the response comprising further evaluating access based on additional criteria.

In one embodiment, any one of the prior systems, wherein the one or more processors are configured by the instructions to determine, or receive an indication of a determination, whether the first computing device can access the information further based on additional criteria, wherein the additional criteria comprises identification from the first and second user data sets of the at least one common user according to a second likelihood function.

In one embodiment, any one of the prior systems, wherein the one or more processors are further configured by the instructions to provide the response based additionally on whether there is the identification of the at least one common user according to the second likelihood function.

In one embodiment, any one of the prior systems, wherein the one or more processors are further configured by the instructions to determine, or receive a determination, that there is a low likelihood of the identification of the at least one common user, wherein the response comprises sharing an anonymized version of the first user data set with the first computing device.

In one embodiment, any one of the prior systems, wherein the one or more processors are further configured by the instructions to determine, or receive a determination, that there is a high likelihood of the identification of the at least one common user, the response comprising removal of data, evaluating whether removal of one or more fields of data prevents the identification, or a denial of the request.

In one embodiment, any one of the prior systems, wherein the one or more processors are configured by the instructions to determine the access alone or in combination with one or more other devices, or the one or more processors are configured by the instructions to receive the indication of the determination of the access from the one or more other devices, wherein the one or more other devices includes the first computing device, at least a second computing device, or a combination of the first and the at least a second computing devices.

In one embodiment, any one of the prior systems, wherein the determination of the access or receipt of the indication of the determination of the access is based on receipt of data from a distributed ledger, based on a multi-party computation method, or based on computations performed in a trusted execution environment.

In one embodiment, any one of the prior systems, wherein the determination of the access or the receipt of the indication of the determination of the access comprises a binary output or a fuzzy output.

In one embodiment, any one of the prior systems, wherein the determination of the access or the receipt of the indication of the determination of the access is based on a determination of a fuzzy function using a third likelihood function, wherein the fuzzy function or the third likelihood function is either pre-set or adaptive.

In one embodiment, any one of the prior systems, wherein the determination of the access or the receipt of the indication of the determination of the access is based on a data driven approach, the data driven approach for use in derivation of rules or training machine-learning models, wherein the data driven approach comprises computation of a score as a function of weights for respective data in the first and second user data sets.

In one embodiment, any one of the prior systems, wherein the response comprises one of: a denial of the request; removal or denial of access of data corresponding to an identifiable user or users from the first user data set, the removal implemented before sharing; removal of a first field of data corresponding to the identifiable user or users from the first user data set, the first field of data comprising a portion that permits the user to be identifiable, the removal implemented before sharing; transmittal of a request to the first computing device for removal of data corresponding to the identifiable user or users from a second user data set, the removal implemented before sharing; transmittal of a request to the first computing device for removal of a second field of data corresponding to the identifiable user or users from the second user data set, the second field of data comprising a portion that permits the user to be identifiable, the removal implemented before sharing; or permitting access to the information based on the criteria comprising consent or permission by the user to access the information.

In one embodiment, any one of the prior systems, wherein the one or more processors are further configured by the instructions to communicate a request to the first computing device to verify the removal of the data or the second field of data from the second user data set or receive a verification of the removal of the data or the second field of data from the second user data set from a distributed ledger.

In one embodiment, a non-transitory computer readable storage medium is disclosed comprising instructions that, when executed by one or more processors, causes the one or more processors to perform the functions of any one of the preceding systems.

In one embodiment, a computer-implemented method is disclosed that comprises steps to perform the functions of any one of the preceding systems.

In one embodiment, a non-transitory computer readable storage medium is disclosed comprising instructions that, when executed by one or more processors, causes the one or more processors to: receive a request from a first computing device for access to information related to a first user data set; determine, or receive an indication of a determination, whether the first computing device can access the information based on criteria for sharing information, the criteria based on one or more characteristics of the first user data set and a second user data set accessible by the first computing device; and provide a response based on the determination, the response preserving privacy of a user corresponding to the first user data set.

In one embodiment, the prior non-transitory computer readable storage medium, wherein the determination or the receipt of the indication of the determination is based on receipt of data from a distributed ledger, based on a multi-party computation method, or based on computations performed in a trusted execution environment.

In one embodiment, a computer-implemented method is disclosed, the method comprising: receiving at an apparatus a request from a first computing device for access to information related to a first user data set; determining, or receiving an indication of a determination, whether the first computing device can access the information based on criteria for sharing information, the criteria based on one or more characteristics of the first user data set and a second user data set accessible by the first computing device; and providing a response based on the determination, the response preserving privacy of a user corresponding to the first user data set.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

The invention claimed is:

1. A system, comprising:
    an apparatus, comprising:
        a communications interface configured to enable communications with one or more computing devices;
        one or more processors configured by instructions to:
            receive a request from a first computing device for access to information related to a first user data set;
            determine, or receive an indication of a determination, whether the first computing device can access the information based on criteria for sharing information, and
            provide a response based on the determination;
        wherein the first user data set comprises an anonymized record that provides privacy of an identification of a user corresponding to the first user data set, and
        wherein the criteria is based on whether according to a likelihood function there is a presence of a common user among the first user data set and a second user data set that is accessible by the first computing device, based on characteristics of the first and second user data sets.

2. The system of claim 1, wherein the criteria is set rules based or fuzzy rules based.

3. The system of claim 1, wherein the criteria comprises adaptive criteria.

4. The system of claim 1, wherein the one or more processors are configured by the instructions to determine the access alone or in combination with one or more other devices, or the one or more processors are configured by the instructions to receive the indication of the determination of the access from the one or more other devices, wherein the one or more other devices includes the first computing device, at least a second computing device, or a combination of the first and the at least a second computing devices.

5. The system of claim 1, wherein the determination of the access or receipt of the indication of the determination of the access is based on receipt of data from a distributed ledger, based on a multi-party computation method, or based on computations performed in a trusted execution environment.

6. The system of claim 1, wherein the determination of the access or the receipt of the indication of the determination of the access comprises a binary output or a fuzzy output.

7. The system of claim 1, wherein the determination of the access or the receipt of the indication of the determination of the access is based on a determination of a fuzzy function using an other likelihood function, wherein the fuzzy function or the other likelihood function is either pre-set or adaptive.

8. The system of claim 1, wherein the determination of the access or the receipt of the indication of the determination of the access is based on a data driven approach, the data driven approach for use in derivation of rules or training machine-learning models, wherein the data driven approach comprises computation of a score as a function of weights for respective data in the first and second user data sets.

9. The system of claim 1, wherein the response comprises one of:
    a denial of the request;
    removal or denial of access of data corresponding to an identifiable user or users from the first user data set, the removal implemented before sharing;
    removal of a first field of data corresponding to the identifiable user or users from the first user data set, the first field of data comprising a portion that permits the user to be identifiable, the removal implemented before sharing;
    transmittal of a request to the first computing device for removal of data corresponding to the identifiable user or users from a second user data set, the removal implemented before sharing;
    transmittal of a request to the first computing device for removal of a second field of data corresponding to the identifiable user or users from the second user data set, the second field of data comprising a portion that permits the user to be identifiable, the removal implemented before sharing; or
    permitting access to the information based on the criteria comprising consent or permission by the user to access the information.

10. The system of claim 9, wherein the one or more processors are further configured by the instructions to communicate a request to the first computing device to verify the removal of the data or the second field of data from the second user data set or receive a verification of the removal of the data or the second field of data from the second user data set from a distributed ledger.

11. The system of claim 1, wherein the determination of whether the first computing device can access the information is to deny access when an output of the likelihood function is above a threshold value.

12. A system, comprising:
    an apparatus, comprising:
        a communications interface configured to enable communications with one or more computing devices;
        one or more processors configured by instructions to:
            receive a request from a first computing device for access to information related to a first user data set;
            determine, or receive an indication of a determination, whether the first computing device can access the information based on criteria for sharing information, the criteria based on one or more characteristics of the first user data set and a second user data set accessible by the first computing device; and provide a response based on the determination, the response preserving privacy of a user corresponding to the first user data set;

wherein the criteria comprises commonality of one or more users associated with the first user data set and the second user data set according to a first likelihood function, wherein the one or more processors are configured by the instructions to determine, or receive the indication of the determination, by:

determining, alone or in combination with one or more other devices, or receiving an indication of a determination from the one or more other devices, whether according to the first likelihood function there is a presence of at least one common user among the first user data set and the second user data set, wherein the determination or receipt of the indication of the determination is based on computations performed on an anonymized version of the first and second user data sets.

13. The system of claim 12, wherein the at least one common user comprises a user identifier, wherein responsive to an absence of the user identifier in one of the first and second user data sets, the response comprises the one or more processors sharing an anonymized version of the first user data set with the first computing device.

14. The system of claim 12, wherein the response is based on the determination or receipt of the indication of the determination of the presence, the response comprising further evaluating access based on additional criteria.

15. The system of claim 12, wherein the one or more processors are configured by the instructions to determine, or receive an indication of a determination, whether the first computing device can access the information further based on additional criteria, wherein the additional criteria comprises identification from the first and second user data sets of the at least one common user according to a second likelihood function.

16. The system of claim 15, wherein the one or more processors are further configured by the instructions to provide the response based additionally on whether there is the identification of the at least one common user according to the second likelihood function.

17. The system of claim 16, wherein the one or more processors are further configured by the instructions to determine, or receive a determination, that there is a low likelihood of the identification of the at least one common user, wherein the response comprises sharing an anonymized version of the first user data set with the first computing device.

18. The system of claim 16, wherein the one or more processors are further configured by the instructions to determine, or receive a determination, that there is a high likelihood of the identification of the at least one common user, the response comprising removal of data, evaluating whether removal of one or more fields of data prevents the identification, or a denial of the request.

19. A non-transitory computer readable storage medium comprising instructions that, when executed by one or more processors, causes the one or more processors to:

receive a request from a first computing device for access to information related to a first user data set;

determine, or receive an indication of a determination, whether the first computing device can access the information based on criteria for sharing information, and provide a response based on the determination;

wherein the first user data set comprises an anonymized record that provides privacy of an identification of a user corresponding to the first user data set, and wherein the criteria is based on whether according to a likelihood function there is a presence of a common user among the first user data set and a second user data set that is accessible by the first computing device, based on characteristics of the first and second user data sets.

20. The non-transitory computer readable storage medium of claim 19, wherein the determination or the receipt of the indication of the determination is based on receipt of data from a distributed ledger, based on a multi-party computation method, or based on computations performed in a trusted execution environment.

21. The non-transitory computer readable storage medium of claim 19, wherein the determination of whether the first computing device can access the information is to deny access when an output of the likelihood function is above a threshold value.

22. A computer-implemented method, comprising:

receiving at an apparatus a request from a first computing device for access to information related to a first user data set;

determining, or receiving an indication of a determination, whether the first computing device can access the information based on criteria for sharing information, and providing a response based on the determination;

wherein the first user data set comprises an anonymized record that provides privacy of an identification of a user corresponding to the first user data set, and wherein the criteria is based on whether according to a likelihood function there is a presence of a common user among the first user data set and a second user data set that is accessible by the first computing device, based on characteristics of the first and second user data sets.

23. The method of claim 22, wherein the determination of whether the first computing device can access the information is to deny access when an output of the likelihood function is above a threshold value.

* * * * *